(12) United States Patent
Taniguchi

(10) Patent No.: US 7,350,961 B2
(45) Date of Patent: Apr. 1, 2008

(54) AGITATION MIXER, PASTEURIZER, AND CLEANING DEVICE

(75) Inventor: Toru Taniguchi, Miyazaki-gun (JP)

(73) Assignee: Reika Kogyo Kabushiki Kaisha, Miyazaki-Gun (JP)

( * ) Notice: Subject to any disclaimer, the term of this patent is extended or adjusted under 35 U.S.C. 154(b) by 495 days.

(21) Appl. No.: 10/896,929

(22) Filed: Jul. 23, 2004

(65) Prior Publication Data

US 2005/0037119 A1 Feb. 17, 2005

(30) Foreign Application Priority Data

Aug. 13, 2003 (JP) .............................. 2003-292785

(51) Int. Cl.
*B01F 11/00* (2006.01)
*B01F 15/02* (2006.01)
(52) U.S. Cl. ................... 366/118; 366/173.1; 366/307; 210/97; 210/194
(58) Field of Classification Search ........ 366/117–119, 366/174.1, 289, 332, 64–66, 192, 255–259, 366/307, 168.1, 171.1, 172.1, 173.1; 210/197, 210/97, 194
See application file for complete search history.

(56) References Cited

U.S. PATENT DOCUMENTS

| 2,604,386 | A | * | 7/1952 | Arant | .......................... 510/405 |
|---|---|---|---|---|---|
| 2,615,692 | A | * | 10/1952 | Muller | ....................... 366/273 |
| 2,667,407 | A | * | 1/1954 | Fenske et al. | ........... 423/658.5 |
| 2,681,798 | A | * | 6/1954 | Muller | ....................... 366/118 |
| 3,318,668 | A | * | 5/1967 | Ziehl | ......................... 422/259 |
| RE26,257 | E | * | 8/1967 | Altman | ....................... 426/508 |
| 3,855,368 | A | * | 12/1974 | Prochazka et al. | ............ 261/81 |
| 4,099,267 | A | * | 7/1978 | King | ........................... 366/142 |
| 4,128,052 | A | * | 12/1978 | Mueller et al. | ................ 99/516 |
| 4,205,094 | A | * | 5/1980 | Baird et al. | .................. 426/459 |
| 4,259,021 | A | * | 3/1981 | Goudy, Jr. | .................... 366/118 |
| 4,737,349 | A | * | 4/1988 | Arnold et al. | ............... 422/226 |
| 4,983,045 | A | * | 1/1991 | Taniguchi | .................... 366/117 |
| 5,178,461 | A | * | 1/1993 | Taniguchi | .................... 366/332 |

(Continued)

FOREIGN PATENT DOCUMENTS

DE 3628012 A1 * 2/1988

(Continued)

*Primary Examiner*—Charles E. Cooley
(74) *Attorney, Agent, or Firm*—Oliff & Berridge, PLC

(57) ABSTRACT

Dissolution of a raw material, fusion of a raw material, or treatment for enhancing the fluidity of a raw material is completed in a short time by an agitation mixer 10 comprising a casing 20 in which a flow channel allowing the passage of fluid is mounted inside, an agitator body 40 mounted inside the casing and connected to a vibration source 46, a material inlet 12 mounted on the lowermost part of the casing 20 to feed the raw material into the casing 20, and a steam feeder 30 for injecting steam into the inside of the casing 20. Agitation chambers 26 divided by partition plates 24 are formed in the casing 20. A pressure gage 32 for measuring injection pressure of the steam is attached to the steam feeder 30. An outlet 14 is mounted on the uppermost part of the casing 20 to eject the raw material after the raw material is treated. Further, one of the agitation chambers 26 to which the outlet 14 is mounted includes a filter 50 placed so as to surround the agitator body 40.

16 Claims, 3 Drawing Sheets

U.S. PATENT DOCUMENTS

| | | | |
|---|---|---|---|
| 5,375,926 A * | 12/1994 | Omasa | 366/118 |
| 5,391,000 A * | 2/1995 | Taniguchi | 366/332 |
| 5,829,873 A * | 11/1998 | King | 366/171.1 |
| 5,904,422 A * | 5/1999 | Kurtz | 366/256 |
| 6,120,176 A * | 9/2000 | Badertscher et al. | 366/147 |
| 6,241,376 B1 * | 6/2001 | Schunemann et al. | 366/99 |
| 6,322,240 B1 * | 11/2001 | Omasa | 366/118 |
| 6,605,252 B2 * | 8/2003 | Omasa | 422/20 |
| 6,655,826 B1 * | 12/2003 | Leanos | 366/119 |
| 7,090,391 B2 * | 8/2006 | Taniguchi | 366/118 |
| 7,293,909 B2 * | 11/2007 | Taniguchi | 366/118 |
| 2001/0000327 A1 | 4/2001 | Zittel et al. | |
| 2003/0070754 A1 | 4/2003 | Francis et al. | |
| 2004/0057332 A1 * | 3/2004 | Taniguchi | 366/118 |
| 2005/0094486 A1 * | 5/2005 | Taniguchi | 366/171.1 |
| 2006/0120212 A1 * | 6/2006 | Taniguchi et al. | 366/118 |
| 2006/0231473 A1 * | 10/2006 | Taniguchi | 210/219 |

FOREIGN PATENT DOCUMENTS

| | | | |
|---|---|---|---|
| DE | 4037957 A1 * | 6/1992 | |
| EP | 1508364 A1 * | 2/2005 | |
| FR | 1.195.160 A | 11/1959 | |
| FR | 1.302.176 A | 8/1962 | |
| GB | 689974 A | 4/1953 | |
| GB | 876070 | * | 8/1961 |
| GB | 994789 | * | 6/1965 |
| JP | 62-125836 | * | 6/1987 |
| JP | 63-44927 | * | 2/1988 |
| JP | 1-231929 | * | 9/1989 |
| JP | 2-43933 | * | 2/1990 |
| JP | 2-293034 | * | 12/1990 |
| JP | 3-157129 | * | 7/1991 |
| JP | 3-258337 | * | 11/1991 |
| JP | 7-51557 | * | 2/1995 |
| JP | 10-328547 | * | 12/1998 |
| JP | 11-57441 | * | 3/1999 |
| JP | 11-169697 | * | 6/1999 |
| JP | 11-226377 | * | 8/1999 |
| JP | 2000-51675 | * | 2/2000 |
| JP | 2000-176270 | * | 6/2000 |
| JP | 2000-246131 | * | 9/2000 |
| JP | 2001-46850 | * | 2/2001 |
| JP | 2001-81326 | * | 3/2001 |
| JP | 2001-106704 | * | 4/2001 |
| JP | 2001-239140 | * | 9/2001 |
| JP | A 2002-59474 | | 2/2002 |
| JP | A 2002-59475 | | 2/2002 |
| JP | A 2002-60495 | | 2/2002 |
| JP | A 2002-62429 | | 2/2002 |
| JP | 2003-1083 | * | 1/2003 |
| JP | 2003-47833 | * | 2/2003 |
| JP | 2004-290837 | * | 10/2004 |
| JP | 2005-58916 | * | 3/2005 |
| JP | 2005-103340 | * | 4/2005 |

* cited by examiner

AGITATION MIXER, PASTEURIZER, AND CLEANING DEVICE

BACKGROUND OF THE INVENTION

1. Field of the Invention

The present invention relates to an agitation mixer in which a raw material is heat-fused or enhanced in fluidity using steam, and relates to a pasteurizer and a cleaning device using steam.

2. Description of the Related Art

In general, when a raw material is fused or dissolved by means of heating, a solvent used for dissolution is supplied into a tank with an agitator in advance or concurrently with feeding of the powder, and then mixed with the powder.

In this method, however, because undissolved substances (i.e. agglomerates or lumps) of the powder are dispersed in the solvent, high volumes of solvent and/or lengthy periods of time are inevitably expended for uniform fusion or uniform dissolution.

For example, when a film is formed by dissolving a polyvinyl alcohol series resin in a solvent and then preparing a resulting undiluted solution through mixing and deaeration, disadvantages that undissolved substances remain due to poor agitation and that distribution of concentration is non-uniform in the solution containing the polyvinyl alcohol series resin can develop during generation of a high concentration of the undiluted solution, which brings about difficulties in controlling the concentration of the undiluted solution to be uniform.

In view of the aforesaid problem, there is suggested a method of preparing an aqueous solution of vinyl alcohol series resin, the method in which a wet cake of hydrated polyvinyl alcohol series resin is dissolved in a dissolver canister with an impeller blade for generating vertical reflux while blowing steam into the dissolver canister (refer to, for example, Japanese Patent Laid-Open Publication No. 2002-60495, No. 2002-59474, No. 2002-59475, and No. 2002-62429).

When the aqueous solution of vinyl alcohol series resin is produced by injecting steam into the wet cake of hydrated polyvinyl alcohol series resin in the dissolver canister (for example, a tank) having the impeller blade as described above, a lengthy period of time is spent for dissolution of the hydrated polyvinyl alcohol series resin.

SUMMARY OF THE INVENTION

It is an advantage of this invention to provide an agitation mixer capable of uniformly dissolving or heat-fusing a powder and enhancing fluidity of a raw material in a short time, a pasteurizer capable of short-time pasteurization and short-time sterilization, and a cleaning device capable of short-time cleaning.

An agitation mixer, pasteurizer, and cleaning device of this invention have the following characteristics.

(1) An agitation mixer comprises a casing in which a flow channel allowing the passage of fluid is formed inside, an agitator body consisting of a shaft installed inside the casing and connected to a vibration source and impeller blades attached to the circumference of the shaft, a material inlet from which a raw material is fed into the casing, and one or more steam inlets from which steam is injected into the inside of the casing.

According to this aspect, by injecting steam directly into the inside of the casing where vibratory agitation is performed, the steam can contact with a raw material in a shorter time compared with a conventional manner of feeding steam while agitating the inside of a tank with impeller blades, which brings about improvement in dissolution, heat-fusion, and fluidity enhancement by heating.

Provision of a plurality of the steam inlets facilitates increasing the rate of contact between the steam and the raw material, which in turn makes it possible to shorten the time required for dissolution, fusion, and fluidity enhancement.

(2) In the agitation mixer according to description (1), one or more agitation chambers are formed inside the casing by dividing the flow channel with partition plates, and the steam inlet is mounted on at least one of the agitation chambers.

Because the steam inlet is provided to each of the agitation chambers, dissolution, fusion, and fluidity enhancement can be performed uniformly in each of the agitation chambers.

(3) In the agitation mixer according to description (1), a filter placed so as to surround the agitator body is installed inside the casing.

By providing the filter, even if undissolved substances or unfused substances (lumps) of a raw material are formed during dissolution and fusion, the undissolved substances or the unfused substances (lumps) are not drained out via the filter and left in the agitation mixer. Accordingly, by re-agitating the inside, the remaining substances can be further dissolved or fused, and thus uniformly dissolved or fused material is obtained.

(4) In the agitation mixer according to any one of descriptions (1) to (3), the raw material is a solid or a powder, and the raw material is heated and/or fused while regulating the amount of steam and/or the pressure of steam.

(5) In the agitation mixer according to any one of descriptions (1) to (3), the raw material is a liquid or a fluid, and the viscosity or reaction of the fluid or the liquid is controlled while regulating the amount of steam and/or the pressure of steam.

(6) This invention provides a pasteurizer using the agitation mixer according to any one of descriptions (1) to (3).

By using the above-described agitation mixer, a substance contained in the casing can be pasteurized or sterilized by steam in a short time.

(7) This invention further provides a cleaning device using the agitation mixer according to any one of descriptions (1) to (3).

(8) In the agitation mixer according to any one of descriptions (1) to (5), the steam is a vapor of either water or a solvent consisting of a single organic solvent or combination of two or more organic solvents.

By selecting a solvent based on dissolution features of a raw material or based on whether or not after-treatment can be easily performed on the solvent and using the selected solvent for the vapor, the raw material can be dissolved or fused uniformly even in a small amount of solvent, which enables production of a high concentration of a solution or a fused material.

(9) In the pasteurizer according to description (6) or the cleaning device according to description (7), the steam is made of water or alcohols.

DESCRIPTION OF THE PREFERRED EMBODIMENTS

Now, embodiments of this invention will be described referring to the attached drawings.

Embodiment 1

Figure 1:
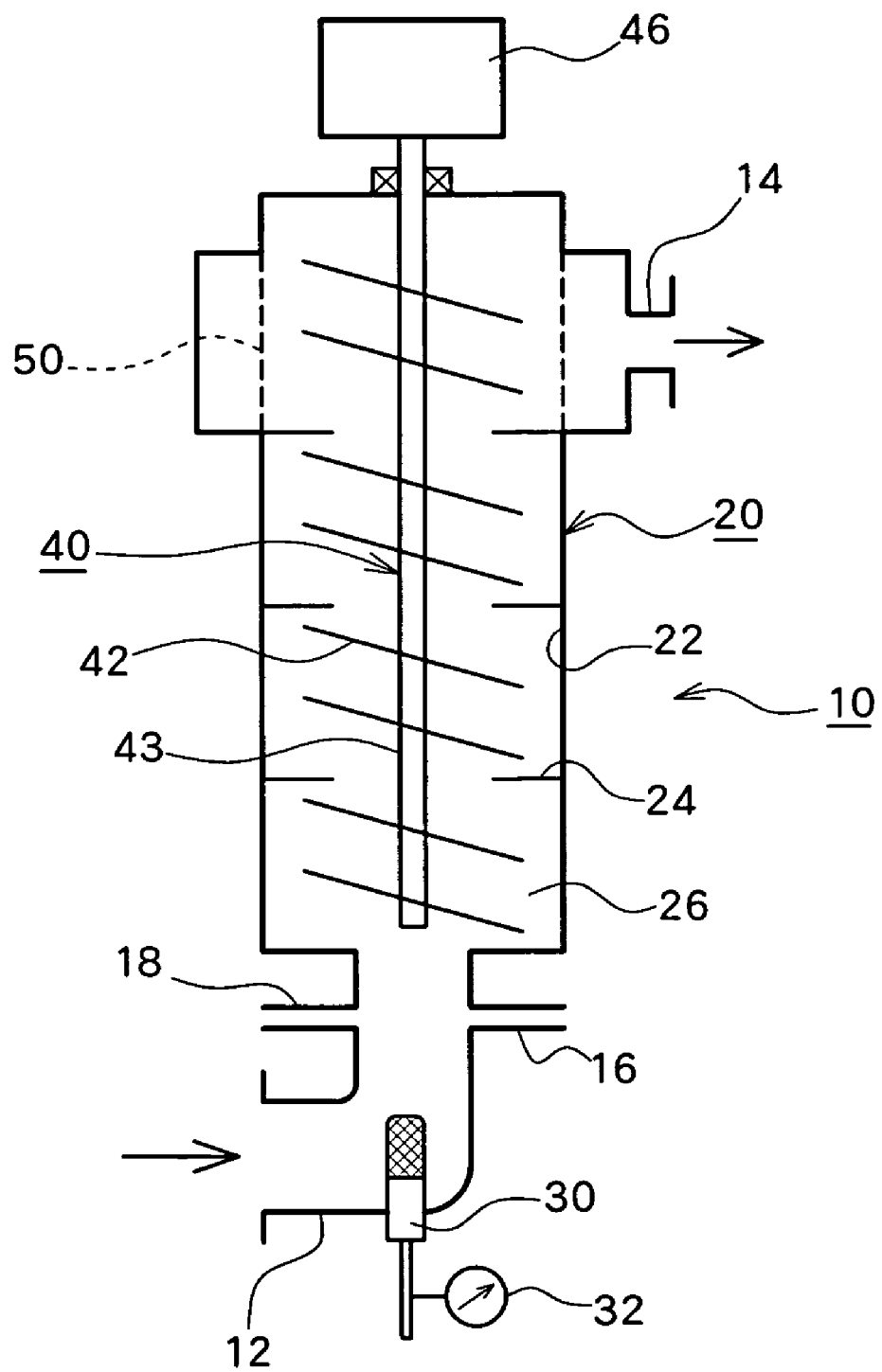
FIG. 1 is a sectional schematic view showing the structure of an agitation mixer according to an embodiment of this invention.

An example structure of the agitation mixer according to a first embodiment will be explained with reference to FIG. 1.

An agitation mixer 10 comprises a casing 20 in which a flow channel allowing the passage of fluid is formed inside, an agitator body 40 consisting of a shaft 43 installed inside the casing 20 and connected to a vibration source 46 and impeller blades 42 attached to the circumference of the shaft 43, a material inlet 12 placed on the lowermost part of the casing 20 to feed a raw material into the inside of the casing 20, and a steam feeder 30 for injecting steam into the inside of the casing 20.

The casing 20 is constructed by a plurality of pipes 22 vertically connected end to end and partition plates 24 inserted in between at each junction of the pipes 22. Further, in the casing 20, agitation chambers 26 separated by the partition plates 24 are formed.

In this embodiment, the steam feeder 30 is placed in the proximity of the material inlet 12, and a pressure gage 32 for measuring injection pressure of steam is attached to the steam feeder 30. Other material inlets 16 and 18 are also provided in the vicinity of the material inlet 12 to feed second and third materials.

An outlet 14 for draining out a treated material when treatment of the raw material is completed is mounted to the uppermost part of the casing 20. Although the material inlet 12 is placed on the lower part of the casing 20 and the outlet 14 is placed on the upper part of the casing 20 in this embodiment, the locations of the inlet 12 and the outlet 14 are not limited to those described above and may be interchanged in a vertical direction.

It should be noted that, in this specification, the term "treatment" is used in a broader sense including dissolution, heating, heat-fusion, heat-melting, fluidity enhancement, reactivity improvement (for example, improvement in reaction rate).

A filter 50 is placed so as to surround the agitator body 40 in one agitation chamber 26 to which the outlet 14 is mounted. Through the use of the filter 50, even if untreated substances (for example, agglomerates or lumps) of a raw material are present in the casing 20, the untreated substances are filtered out so that only treated material can be delivered from the outlet 14. On the other hand, the untreated substances (for example, agglomerates or lumps) of the raw material are agitated again in the agitation mixer 10. For example, a filtering member made of stainless steel or a ceramic having a mesh size in the order of microns (fine mesh), a reverse osmosis membrane, a polymer membrane (nanofilter membrane), etc. may be used for the filter 50.

Next, operation of the agitation mixer 10 according to this embodiment will be described. Here, taking a polyvinyl alcohol resin powder (hereinafter referred to as "PVA powder") as a raw material, the operation is explained in connection with an example method of dissolving the PVA powder to produce a high concentration of a solution.

The PVA powder is fed from the material inlet 12 into the casing 20 in which the agitator body 40 driven by the vibration source 46 is vibrating up and down, whereas steam is injected from the steam feeder 30 concurrently with feeding of the PVA powder. Here, the amount of steam injected from the steam feeder 30 may preferably be specified to a volume necessary for a desired high concentration of a solution and allowing the PVA powder inside the casing 20 to reach a temperature sufficient for dissolving the PVA powder. Further, by regulating the injection pressure of steam continuously measured by the pressure gage 32, the PVA powder can be dissolved in a shorter time even though the amount of steam is not increased. For example, by raising the injection pressure, the steam which causes the PVA powder to dissolve can be set to a substantially higher temperature than the temperature set at normal pressure.

In the casing 20, the PVA powder is entrained and upwardly transported by steam through the agitation chambers 26, and then dissolved by heat. As a result of heat dissolution, the PVA powder is transformed into a high concentration of a PVA solution, which is filtered by the filter 50, and finally drained out from the outlet 14.

In the agitation mixer according to this embodiment, the time elapsed from feeding of the PVA powder to formation of a high concentration of the PVA solution is approximately 15 seconds. Thus, the agitation mixer can significantly shorten the time required for the treatment compared with a conventional steam feeding device for injecting steam into a tank with impeller blades.

Embodiment 2

Figure 2:
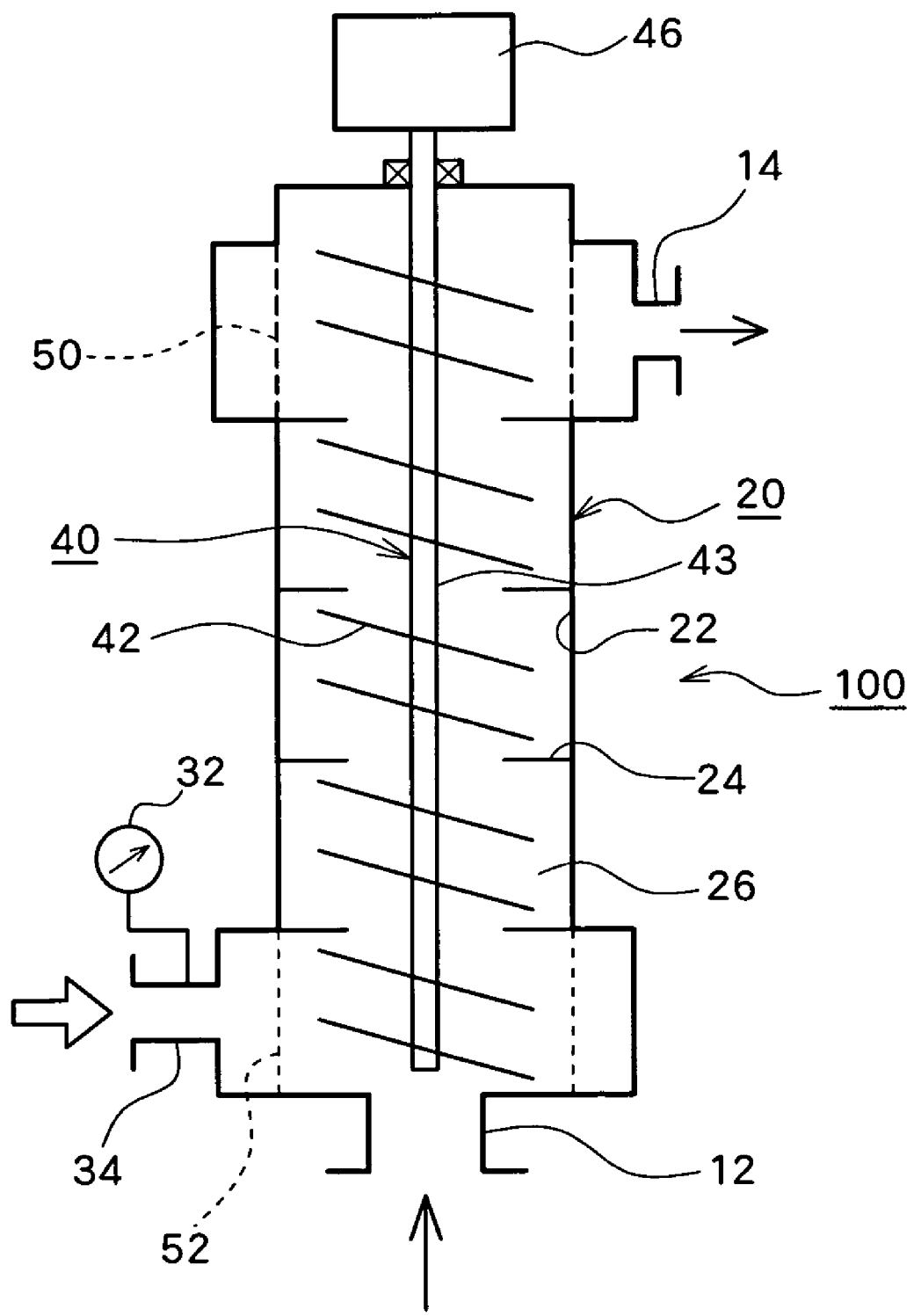
FIG. 2 is a sectional schematic view showing the structure of an agitation mixer according to another embodiment of this invention.

Referring to FIG. 2, another structure of the agitation mixer according to a second embodiment of this invention will be discussed below. Here, components similar to those described in the previous embodiment are identified by the same reference numerals and their description is not repeated.

An agitation mixer 100 comprises the casing 20 in which a flow channel allowing the passage of fluid is formed inside, the agitator body 40 consisting of the shaft 43 installed inside the casing 20 and connected to the vibration source 46 and impeller blades 42 attached to the circumference of the shaft 43, the material inlet 12 placed on the lowermost part of the casing 20 to feed a raw material into the inside of the casing 20, and a steam inlet 34 from which steam is injected into the inside of the casing 20.

In this embodiment, the steam inlet 34 is mounted to the lowest stage of the casing 20, and a filter 52 is placed so as to surround the agitator body 40 in one agitation chamber 26 to which the steam inlet 34 is mounted. In this manner, steam is fed to the inside of the casing 20 through the filter 52 in the form of a uniform mist having a desired size converted by the filter 52. In addition, the pressure gage 32 for measuring injection pressure of steam is attached to the steam inlet 34.

The outlet 14 from which a treated material is ejected when treatment of the raw material is completed is mounted to the uppermost part of the casing 20. Although the material inlet 12 is placed on the lower part of the casing 20 and the outlet 14 is placed on the upper part of the casing 20 in this embodiment, the locations of the inlet 12 and the outlet 14 are not limited to those described above and may be interchanged in a vertical direction as described above.

Further, the filter 50 is also placed so as to surround the agitator body 40 in one agitation chamber 26 to which the outlet 14 is mounted. Through the use of the filter 50, even if untreated substances (for example, agglomerates or lumps) of a raw material are present in the casing 20, the untreated substances are filtered out so that only treated material can be delivered from the outlet 14. On the other hand, the untreated substances (for example, agglomerates or lumps) of the raw material are agitated again in the agitation mixer 100. For example, a filtering member made of stainless steel or a ceramic having a mesh size in the order of microns (fine mesh), a reverse osmosis membrane, a polymer membrane (nanofilter membrane), etc. may be used for the filters 50 and 52.

Next, operation of the agitation mixer 100 according to the second embodiment will be described. Similarly to the previous embodiment, taking a PVA powder as a raw material, the operation is explained in connection with an example method of dissolving the PVA powder to produce a high concentration of a PVA solution.

The PVA powder is fed from the material inlet 12 into the casing 20 in which the agitator body 40 driven by the vibration source 46 is vibrating up and down, whereas steam is injected from the steam inlet 34 concurrently with feeding of the PVA powder. Here, the steam is converted into the uniform mist passing through the filter 52 and fed into the inside of the casing 20 in the form of the uniform mist. The amount of steam injected from the steam inlet 34 may preferably be specified to a volume necessary for a desired high concentration of the solution and allowing the PVA powder inside the casing 20 to reach a temperature sufficient for dissolving the PVA powder. Further, by regulating the injection pressure of steam continuously measured by the pressure gage 32, the PVA powder can be dissolved in a shorter time even though the amount of steam is not increased.

In the casing 20, the PVA powder is entrained and upwardly transported by steam through the agitation chambers 26, and dissolved by heat. As a result of heat dissolution, the PVA powder is transformed into a high concentration of a uniform PVA solution, which is filtered by the filter 50 and finally delivered out from the outlet 14.

Also in the agitation mixer according to this embodiment, the time elapsed from feeding of the PVA powder to formation of a high concentration of the PVA solution is approximately 15 seconds. Thus, the agitation mixer can significantly shorten the time required for the treatment compared with the above-described conventional device.

Embodiment 3

Figure 3:
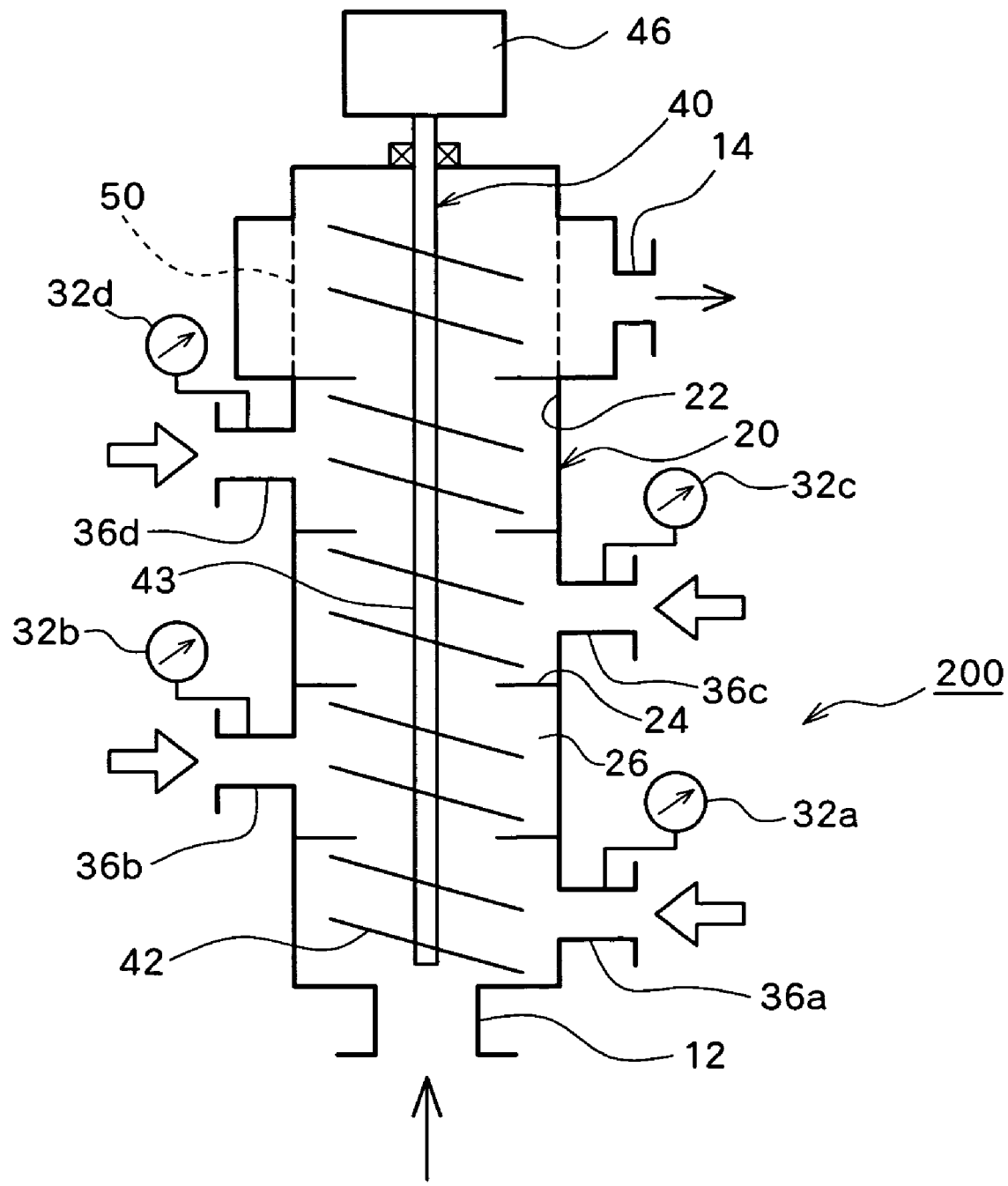
FIG. 3 is a sectional schematic view showing the structure of an agitation mixer according to still another embodiment of this invention.

Referring to FIG. 3, still another structure of the agitation mixer according to a third embodiment of this invention will be discussed below. As above, components similar to those described in the previous embodiments are identified by the same references and their description is not repeated.

An agitation mixer 200 comprises the casing 20 in which a flow channel allowing the passage of fluid is formed inside, the agitator body 40 consisting of the shaft 43 installed inside the casing 20 and connected to the vibration source 46 and impeller blades 42 attached to the circumference of the shaft 43, and the material inlet 12 placed on the lower part of the casing 20 to feed a raw material into the inside of the casing 20.

In this embodiment, a steam inlet 36a, 36b, 36c, or 36d is mounted to each of the agitation chambers 26 in the casing 20 to individually inject steam into the agitation chambers 26. Pressure gages 32a, 32b, 32c, and 32d for measuring injection pressure of steam are attached to the steam inlets 36a, 36b, 36c, and 36d, respectively.

Further, the outlet 14 from which a treated material is ejected when treatment of the raw material is completed is mounted to the uppermost part of the casing 20. Although the material inlet 12 is placed on the lower part of the casing 20 and the outlet 14 is placed on the upper part of the casing 20 in this embodiment, the locations of the inlet 12 and the outlet 14 are not limited to those described above and may be interchanged in a vertical direction as described above.

Further, the filter 50 is placed so as to surround the agitator body 40 in one agitation chamber 26 to which the outlet 14 is mounted. Through the use of the filter 50, even if untreated substances (for example, agglomerates or lumps) of a raw material are present in the casing 20, the untreated substances are filtered out so that only treated material can be delivered from the outlet 14. On the other hand, the untreated substances (for example, agglomerates or lumps) of the raw material may be agitated again in the agitation mixer 200.

For example, a filtering member made of stainless steel or a ceramic having a mesh size in the order of microns (fine mesh), a reverse osmosis membrane, a polymer membrane (nanofilter membrane), etc. may be used for the filter 50 as in the case of the previous embodiments.

Next, operation of the agitation mixer 200 according to this embodiment will be described. Similarly to the previous embodiments, taking the PVA powder as the raw material, the operation is explained in connection with an example method of dissolving the PVA powder to produce a high concentration of the PVA solution.

The PVA powder is fed from the material inlet 12 into the casing 20 in which the agitator body 40 driven by the vibration source 46 is vibrating up and down, whereas steam is injected from the steam inlets 36a, 36b, 36c, and 36d concurrently with feeding of the PVA powder. The amounts of steam injected from the steam inlets 36a, 36b, 36c, and 36d may preferably be specified, as in the case with the previous embodiments, to a volume necessary for a desired high concentration of the PVA solution and allowing the PVA powder inside the casing 20 to reach a temperature sufficient for dissolving the PVA powder. The amounts of steam fed from the steam inlets 36a, 36b, 36c, and 36d may be equal to each other, or may differ from each other. Further, by regulating the injection pressures of steam continuously measured by the pressure gages 32a, 32b, 32c, and 32d, the PVA powder can be dissolved in a shorter time even though the total amount of steam is not increased.

In the casing 20, the PVA powder is entrained and upwardly transported by steam fed from the steam inlets 36a, 36b, 36c, and 36d mounted to the agitation chambers 26, and dissolved by heat. As a result of heat dissolution, the PVA powder is transformed into a high concentration of a uniform PVA solution, which is filtered by the filter 50 and finally delivered out from the outlet 14.

According to this embodiment, because the entire internal space of the casing 20 is evenly maintained at a constant temperature by the steam injected from the steam inlets 36a, 36b, 36c, and 36d separately mounted to each of the agitation chambers 26, the above-described time elapsed from feeding of the PVA powder to formation of a high concentration of the PVA solution can be shortened further from the 15 seconds indicated in the previous embodiments. Although the steam inlet is provided to every one of the agitation chambers 26, provision of the steam inlet is not limited to this manner. The steam inlet may be mounted to alternate agitation chambers 26 or mounted only to a lower set of the successive agitation chambers.

Although an ingredient of the steam used in the agitation mixers according to the above-described embodiments is not specifically specified in the above description, the ingredient of the steam may be made of, but not limited to, water vapor. For example, a solvent suitably compatible with a powder may be selected as appropriate for use in the steam, and two or more solvents may be utilized in combination. Further, dissolving a powder was taken as an example of application in the above description regarding Embodiments 1 to 3. However, application of this invention is not limited to the example, and taking a liquid or a fluid as the raw material, the viscosity of the raw material may be depressed to enhance the fluidity thereof. In this case, the fluidity of the liquid or the fluid may be controlled by injecting steam into the inside of the casing 20 to increase an internal temperature of the casing 20. After reaching desired fluidity, the liquid or the fluid may be ejected from the outlet 14. The agitation mixer according to any one of Embodiments 1 to 3 may be used for heat fusion or heat melting of a powder using steam.

Embodiment 4

A forth embodiment of this invention will be described below. In this embodiment, the agitation mixers described in the above embodiments and illustrated in FIGS. 1 to 3 can be used as a pasteurizer or a cleaning device.

In use as a pasteurizer or a cleaning device, it is preferable that a subject material to be pasteurized is fed into the inside of the casing 20 from the material inlet 12, and water vapor or vapor of alcohols is injected as steam from the steam feeder 30 (shown in FIG. 1), the steam inlet 34 (shown in FIG. 2), or a set of the steam inlets 36a, 36b, 36c, and 36d (shown in FIG. 3).

By configuring the pasteurizer as described above, the subject material to be pasteurized is pasteurized or sterilized in each of the agitation chambers 26 by heat of the steam or, if the steam is made of alcohols, by bactericidal action of alcohols in addition to heat of the steam while moving upward, and collected from the outlet 14 as a pasteurized material. It is preferable to appropriately select the mesh size of the filter 50 according to a grain size of the subject material to be pasteurized.

On the other hand, by configuring the cleaning device as described above, a subject material to be cleaned is exposed to the heat of steam, or, if the steam is made of alcohols, brought into contact with the alcohols as well as being exposed to the heat of steam. Through either or both of the exposure to the heat and the contact with the alcohols, impurities occurring on the surface or in the inside of the subject material to be cleaned are vaporized by the heat of steam, or cleaned by the alcohols as well as, in some cases, being azeotroped with the alcohols when the steam consists of alcohols. In this manner, the subject material to be cleaned is delivered upward while being isolated form the impurities in the casing 20, and the isolated subject matter and the impurities are finally collected at different times from the outlet 14. Also in this case, it is preferable to appropriately select the mesh size of the filter 50 according to a grain size of the subject material to be cleaned.

The agitation mixer of this invention may be applied to uses for dissolving a powder in a small amount of a solvent, for heat-fusing or heat-melting a powder, for depressing the viscosity of a liquid or a fluid to enhance the fluidity thereof, and for increasing the rate or the efficiency of reaction of a liquid or a fluid. In addition to the above-described uses, the agitation mixer of this invention may be used for removing unreacted monomers remaining after polymerizing monomers and a solvent used for polymerization through azeotropy using steam.

What is claimed is:

1. An agitation mixer comprising:
   a casing in which a flow channel allowing the passage of fluid is mounted inside;
   an agitator body comprising a shaft formed inside the casing and connected to a vibration source and impeller blades attached to the circumference of the shaft;
   a material inlet from which a raw material is fed into the casing;
   a material outlet;
   one or more steam inlets from which steam is injected into the inside of the casing; and
   a filter installed inside the casing so as to surround the agitator body,
   wherein one or more agitation chambers are formed inside the casing by dividing the flow channel with partition plates,
   at least one of the one or more steam inlets is positioned in proximity of the material inlet,
   the material outlet is mounted to a first agitation chamber, and
   the filter is placed so as to surround the agitator body in only the first agitation chamber.

2. An agitation mixer according to claim 1, wherein the at least one of the one or more steam inlets is mounted to at least one of the agitation chambers.

3. An agitation mixer according to claim 2, wherein the raw material is either a solid or a powder, and heating and/or fusion of the raw material are performed while regulating the amount of steam and/or the pressure of steam.

4. An agitation mixer according to claim 2, wherein the raw material is either a liquid or a fluid, and the viscosity or reaction of the liquid or the fluid are controlled while regulating the amount of steam and/or the pressure of steam.

5. A pasteurizer using the agitation mixer according to claim 2.

6. A cleaning device using the agitation mixer according to claim 2.

7. An agitation mixer according to claim 2, wherein the steam is either a water vapor or a solvent vapor made of a single organic solvent or combination of two or more organic solvents.

8. An agitation mixer according to claim 1, wherein the raw material is either a solid or a powder, and heating and/or fusion of the raw material are performed while regulating the amount of steam and/or the pressure of steam.

9. An agitation mixer according to claim 1, wherein the raw material is either a liquid or a fluid, and the viscosity or reaction of the liquid or the fluid are controlled while regulating the amount of steam and/or the pressure of steam.

10. A pasteurizer using the agitation mixer according to claim 1.

11. A pasteurizer according to claim 10, wherein the steam is made of water or alcohols.

12. A cleaning device using the agitation mixer according to claim 1.

13. A cleaning device according to claim 12, wherein the steam is made of water or alcohols.

14. An agitation mixer according to claim 1, wherein the steam is either a water vapor or a solvent vapor made of a single organic solvent or combination of two or more organic solvents.

15. An agitation mixer according to claim 1, further comprising a second filter installed inside the casing so as to surround the agitator body,
    wherein the material inlet and the at least one steam inlet positioned in proximity of the material inlet are mounted to a second agitation chamber, and
    the second filter is placed so as to surround the agitator body in only the second agitation chamber.

16. An agitation mixer according to claim 1, wherein at least one of the one or more steam inlets is mounted to each of the one or more agitation chambers.

* * * * *